United States Patent [19]  [11]  4,412,991
Ormond  [45]  Nov. 1, 1983

[54] 22-HYDROXY DERIVATIVES OF C-076 COMPOUNDS, PHARMACEUTICAL COMPOSITIONS AND METHOD OF USE

[75] Inventor: Robert E. Ormond, Edison, N.J.

[73] Assignee: Merck & Co., Inc., Rayway, N.J.

[21] Appl. No.: 297,442

[22] Filed: Aug. 28, 1981

[51] Int. Cl.³ .................... A61K 31/71; C07H 17/08; C12P 19/62

[52] U.S. Cl. ................................ 424/180; 424/181; 435/76; 536/7.1

[58] Field of Search .................... 424/181, 180; 536/4, 536/17 R, 7.1

[56] References Cited

U.S. PATENT DOCUMENTS 4,199,569  4/1980  Chabala et al. .................. 536/17 C
4,206,205  6/1980  Mrozik et al. .................... 424/180

FOREIGN PATENT DOCUMENTS 2387231  11/1978  France ................................ 536/7.1
1573955  8/1980  United Kingdom .

*Primary Examiner*—Johnnie R. Brown
*Attorney, Agent, or Firm*—David L. Rose; Mario A. Monaco

[57] ABSTRACT

There is disclosed novel derivatives of C-076 compounds wherein the 22-position, normally substituted, is substituted with a hydroxy group. The compounds are isolated from the C-076 fermentation broth of *Streptomyces avermitilis*. The compounds have potent anthelmintic, insecticidal, and acaricidal activity and compositions for that use are also disclosed.

5 Claims, No Drawings

22-HYDROXY DERIVATIVES OF C-076 COMPOUNDS, PHARMACEUTICAL COMPOSITIONS AND METHOD OF USE

BACKGROUND OF THE INVENTION

The C-076 family of compounds are a series of macrolides isolated from the fermentation broth of a strain of *Streptomyces avermitilis*. The C-076 compounds are characterized by having a 16-membered cyclic backbone substituted with a disaccharide and having a bicyclic spiroketal fused thereon. The compounds have the structure:

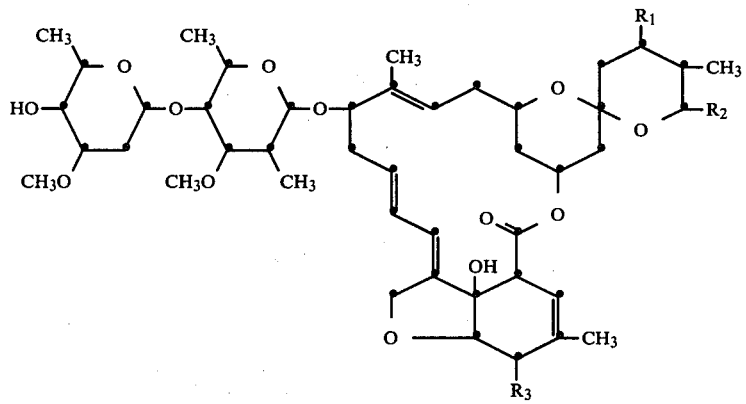

wherein the broken line indicates a single or a double bond;

$R_1$ is hydroxy and is present only when said broken line indicates a single bond;

$R_2$ is iso-propyl or sec-butyl; and $R_3$ is methoxy or hydroxy.

The C-076 compounds are named using a system of designations which corresponds to the structural variations as is set forth in the following table.

| Compound | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

The above compounds are isolated from the fermentation broth of *Streptomyces avermitilis* using normal extraction and isolation procedures. The C-076 producing culture and the morphological characteristics thereof along with the procedures used for separating and isolating the C-076 compounds, are fully described in Great Britain Patent 1573955, published Aug. 28, 1980.

The fermentation is carried out in an aqueous medium and includes an assimilable source of carbon, an assimilable source of nitrogen and inorganic salts and the fermentation is generally carried out under aerobic conditions. The specific nutrients and parameters for the fermentation are described completely in the above cited Great Britain Patent.

The C-076 producing culture and a mutant thereof have been deposited in the permanent culture collection of the American Type Culture Collection, 12301 Parklawn Drive, Rockville, Md. 20852. The cultures are accessible under the accesion numbers ATCC 31267 for the basic culture and ATCC 31272 (lyophilized tube) and ATCC 31271 (frozen vial) for the mutant. The C-076 compounds are potent antiparasitic agents with very broad spectrum anthelmintic, acaricidal, nematocidal and insecticidal activity.

SUMMARY OF THE INVENTION

The instant invention is concerned with novel C-076 derivatives and procedures for their isolation from the fermentation broth of a C-076 producing strain of *Streptomyces avermitilis*. Thus, it is an object of this invention to describe such novel C-076 derivatives. It is a further object of this invention to describe the processes for their isolation from fermentation broths. A still further object is to describe the antiparasitic effects of such novel compounds. Further objects will become apparent from a reading of the following description.

DESCRIPTION OF THE INVENTION

The novel compounds of this invention are best described in the following structural formula:

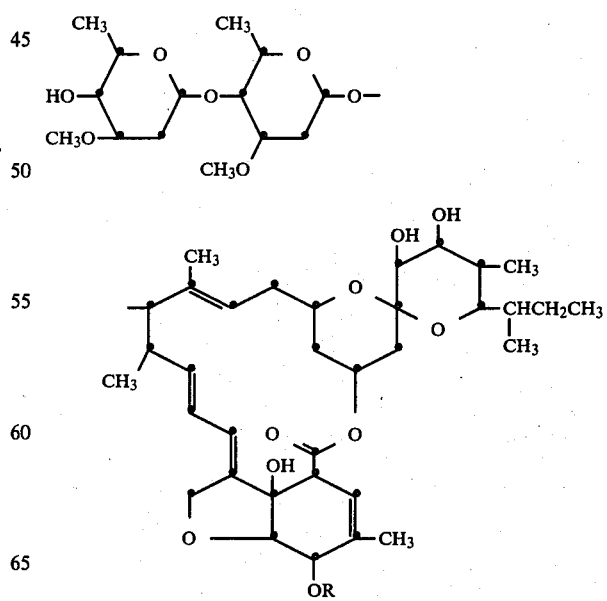

wherein R is hydrogen or methyl.

From an analysis of the foregoing compounds, they are seen to be similar to the parent C-076 compounds, but with some very major differences.

The difference between the C-076 starting materials and the instant compounds is in the latter compounds having an additional hydroxy group at the 22-position. Such compounds are not suggested by the parent C-076 compounds and no procedures are provided by which such compounds could be made.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such s swine, sheep, horses, cattle, goats, dogs, cats and poultry. Among the helminths, the group of worms described as nematodes causes widespread and often times serious infection in various species of animals. The most common genera of nematodes infecting the animals referred to above the Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly Musca domestica.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasties such as Meloidogyne spp. which may be of importance in agriculture.

These compounds may be administered orally in unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the C-076 compounds in a dry, solid unit dosage form, capsules, boluses or tablets containing the desired amount of active compound usually are employed. These dosage forms ae prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which even the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active C-076 compound or compounds are dissolved or suspended in the parenteral formulation for administration; such formulations generally contain from 0.005 to 5% by weight of the active compound. Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 compound employed, the compounds of this invention are usually fed at concentrations of between 0.00001 to 0.002% in the feed in order to achieve the desired antiparasitic result.

In using the compounds of this invention, the individual C-076 components may be isolated and purified and used in that form. Alternatively, mixtures more of the individual C-076 components may be used. It is not necessary to completely separate the various C-076 compounds obtained from the purification of the fermentation broth. Occasionally, there is obtained a mixture containing two or more of the C-076 compounds, but having other unrelated compounds excluded therefrom, and such mixture may be used for the prevention and treatment of parasitic diseases as described herein. Such a mixture generally will contain unequal proportions of the C-076 compounds, however, all of the compounds have substantial activity and the antiparasitic activity of the mixture can be accurately determined.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are isolated from the fermentation broth of *Strepomyces avermitilis* in smaller amounts than the parent C-076 compounds. However, substantially similar processes are used to isolate such compounds. The standard techniques for extraction and purification, known to those skilled in the art, are employed to purify the instant compounds. The techniques of solvent extraction, column chromatography, thin layer chromatography, preparative layer chromatography, high pressure liquid chromatography and the like are useful for the isolation and purification of the instant compounds. The technique employed generally consists of separating extracts containing the A and B compounds, crystallizing the B compounds to remove the C-076 B compounds and processing the crystallization mother liquors on columns to isolate the compounds of this invention.

The following examples describe the fermentation and the isolation and purification procedures for the preparation of the instant compounds. The examples are provided in order that the invention might be more fully understood. They should not be construed as limitative of the invention.

EXAMPLE 1

A 250-ml baffled Erlenmeyer flask containing 50 ml of the following medium:

| | |
|---|---|
| Lactose: | 2.0% |
| Distiller's Solubles: | 1.5% |
| Autolyzed yeast, Ardamine pH: | 0.5% |
| pH-before sterilization: | 7.0 | is inoculated with the contents of one frozen vial of *Streptomyces avermitilis* MA-4848 and incubated on a rotary shaker at 28° C. for 24 hours at 150 rpm.

Ten ml of the above fermentation medium is employed to inoculate 500 ml of the same medium as above in a 2-liter baffled Erlenmeyer flask. The fermentation medium is incubated at 150 rpm on a rotary shaker at 28° C. for 24 hours.

All of the foregoing medium is employed to inoculate 467 liters of the following medium in a 756-liter stainless steel fermentor:

| | |
|---|---|
| Lactose: | 2.0% |
| Distiller's Solubles: | 1.5% |
| Autolyzed yeast, Ardamine pH: | 0.5% |
| Polyglycol 2000: 0.32 ml/liter | |
| pH-before sterilization: | 7.0 |

The fermentation medium is incubated at 28° C. for 40 hours with an air flow of 10 cubic feet per minute and an agitation rate of 130 rpm.

230 Liters of the above medium is employed to inoculate 4,310 liters of the following medium in a 5,670-liter stainless steel fermentor:

| | |
|---|---|
| Dextrose: | 4.5% |
| Peptonized Milk: | 2.4% |
| Autolyzed yeast, Ardamine pH: | 0.25% |
| Polyglycol 2000: 2.5 ml/liter | |
| pH-before sterilization: | 7.0 |

The fermentation continues for 144 hours at 26° C. with an air flow rate of 54.3 cubic feet per minute and agitation rate of 120 rpm. The foregoing fermentation procedures are carried out again on the same scale, and the broths are combined just prior to the next (filtration) step.

The fermentation media of the foregoing described fermentations are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water and combined with the first extract affording about 2000 liters of combined extract. The acetone extract is evaporated to a volume of about 800 liters. The pH of the concentrate is adjusted to about 4.7 with concentrated hydrochloric acid and combined with about 400 liters of methylene chloride. The combined solvents are agitated for about 4 hours and separated. The aqueous layer is combined with an additional 400 liters of methylene chloride and agitated for about 4 hours. The layers are separated and each methylene chloride extract separately treated with about 10 kilograms of Super-Cel and filtered. Both extracts are evaporated to a combined volume of about 40 liters.

The foregoing fermentation steps are repeated to obtain a second 40 liter extract. This extract is not combined with the first extract at this time.

EXAMPLE 2

The 40-liter solution of C-076 in methylene chloride of the previous example is concentrated to dryness in vacuo and the residue in combined three times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2-layer solution is agitated for 5 minutes and the lower layer (ethylene glycol and methanol) is separated. The heptane solution is washed with a mixture of 20 liters of ethylene glycol and 6.3 liters of methanol. After 5 minutes of agitation, the lower layer is separated and combined with the first ethylene glycol/methanol extract. An equal volume of water (approximately 150 liters) containing 79 g of salt per liter is added to the ethylene glycol/methanol extracts. This solution is extracted with 150 liters of ethyl ether with agitation for 5 minutes. The ether layer is washed with 75 liters of water (½ volume) and agitated for 5 minutes and the layers separated. This procedure is repeated an additional 2 times (the final water wash contains 20 g of salt per liter) affording a final ether layer volume of 150 liters. The ether layer is concentrated in vacuo, to a minimum volume, keeping the temperature less than 25° C. Forty liters of methylene chloride is added to the residue and the solution is evaporated to dryness. This procedure is repeated and the final residue concentrated in vacuo at 50° C. to dryness.

The foregoing procedures are repeated on the second 40 liter extract from Example 1.

EXAMPLE 3

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. These fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

The foregoing procedure is repeated on the second residue obtained from Example 2 to obtain a second 15 liter extract. This material is processed as described in Example 6.

EXAMPLE 4

A 30 centimeter diameter column is prepared in methanol with 36 kilograms of Sephadex LH-20 (available from Pharmacia Fine Chemicals, 800 Centennial Avenue, Piscataway, N.J. 08854) and washed with a solvent consisting of 10 parts methylene chloride, 10 parts hexane and one part methanol. One-half of the C-076 solutions of Example 3 is applied to the column and the column eluted at a rate of 250 ml per minute. Two 20 liter forecuts are collected and discarded followed by 20 two liter rich cuts (identified as fractions 1–20), followed by a single 20 liter tail cut, which is discarded. Fractions 2–6 are found to contain the C-076 A compounds and fractions 9–20 are found to contain the c-076 B compounds. The procedure is repeated on the second half of the 15 liter extract to obtain an additional series of fractions rich in B compounds.

EXAMPLE 5

In the two Sephadex LH-20 columns of the procedure of Example 4, fractions 10–18 from the first column and 9–16 from the second are combined. By HPLC analysis the mixture is found to contain 129 g of C-076 B1a, 18 g B1b, 83.5 g B2a and 3 g of B2b.

This material is dissolved in 3 liters of a solvent mixture of hexane:toluene:methanol in the ration of 3:1:1. The solution is passed through a column of Sephadex LH-20 (having a 30 centimeter diameter) in the above solvent taking fractins at the rate of 250 ml per minute. After two 20-liter portions of the solvent mixture are collected and discarded. A forecut of 20 liters is taken (identified as FC-3). Rich cuts are then taken as follows: 5 cuts of 2 liters each (fractions 1–5); 20 cuts of 1 liter each (fractions 6–25); and 20 cuts 2 liters each (fractions 26–45).

EXAMPLE 6

A 30 centimeter diameter column is prepared in methanol with 36 kilograms of Sephadex LH-20 (available from Pharmacia Fine Chemicals, 800 Centennial Avenue, Piscataway, N.J. 08854) and washed with a solvent consisting of 10 parts methylene chloride, 10 parts hexane and one part methanol. The entire second 15 liter extract of the C-076 solution of Example 3 is applied to the column and the column eluted at a rate of 250 ml per minute. Two 20 liter forecuts are collected an discarded followed by 20 two liter rich cuts (identified as fractions 1-20), followed by a single 20 liter tail cut, which is discarded. Fractions 3-14 are found to contain the C-076 A compounds and fractions 15-19 are found to contain the C-076 B compounds.

EXAMPLE 7

Fractions 15-19 of Example 6 are concentrated to dryness (68 grams). By HPLC analysis the mixture is found to contain 41.7 g of C-076 B1a, 11.4 g B1b, and 13.2 g B2a. The mixture is dissolved in 340 ml of absolute ethyl alcohol. After crystallization had started, it is stirred with a magnetic stirrer at 0° C. The crystals are filtered, washed with 1/10 original volume of cold absolute ethyl alcohol and cold 95% ethyl alcohol. The mother liquor and washes are combined and concentrated in vacuo. The mother liquors are further processed in Example 10 after combining with other mother liquors.

EXAMPLE 8

C-076 B1 material is crystallized from fractions of Example 5. Forecut 3, fractions 1-12, fractions 13-24, fractions 25-38 and fractions 39-45 by the same method employed in Example 7.

|  | wt. | B1a | B1b | B1 | B2 |
| --- | --- | --- | --- | --- | --- |
| FC-3 | 6.4 g | 91% | 1.4% | 92.4% |  |
| 2nd crop | 0.8 g | 86.8% | 2.4% | 89.2% |  |
| 1-12 | 42.7 g | 90.7% | 7.2% | 97.9% | 0.4 |
| 2nd crop | 6.0 g | 79.1 | 13.8 | 92.9% | 2.2 |
| 13-24 | 25.3 g | 81.7 | 12.8 | 94.5% | 4.5 |
| 2nd crop | 1.7 g | 74 | 12.9 | 86.9% | 11.5 |
| 25-38 | 17.7 g | 75.8 | 12.8 | 88.6% | 10.7 |
| 39-45 | 17.0 g | 76.4 | 10.4 | 86.8 | 12.3 |

The C-076 B2 rich mother liquors are combined and crystallized to remove any additional C-076 B1. The mother liquors are further processed in Example 10 after conbining with other mother liquors.

EXAMPLE 9

The two first crop crystalline products from Example 8 (FC-3) and (1-12) are combined (49.2 g), dissolved in 2 liters of a solvent mixture of hexane:toluene:methanol in the ratio of 3:1:1. The solution is passed through a column of Sephadex LH-20 (of the same dimensions as the one used in Example 6). After three 20 liter cuts are collected and discarded five 2 liter, 20 1 liter and 20 2 liter rich cuts are taken. Fractions 1-20 and 43-45 are discarded. The C-076 B1 rich cuts are pooled in five parts, fractions 21-24, 25-28, 29-31, 32-35 and 36-42 and crystallized in the same manner as Example 7. The C-076 B1 spent mother liquors are combined and crystallized for additional B1 removal. The mother liquors are further processed in Example 10 after combining with other mother liquors.

EXAMPLE 10

The C-076 B1 spent mother liquors rich in C-076 B2 obtained from Example 7, Example 8 and Example 9 are combined and dried. 131 Grams consisting of 87.6 g of C-076 B2a and 9.9 g of B1a is dissolved in 2300 ml of a solvent mixture of hexane:toluene:methanol in the ratio of 3:1:1. This solution is then chromatographed on Sephadex LH-20 (30 cm diameter column) equilibrated with hexane:toluene:methanol in the ratio of 6:1:1. The column is then developed with the 6:1:1 solvent at the rate of 250 ml per minute. After 6-20 liter forecuts are taken and discarded, 3 10 liter and 40 3 liter rich cuts are collected.

Fractions 34-41 are combined (4.2 g 59% B2a by weight) and crystallized from 10 ml of toluene at from 0°-4° C. The crystals are suspended in an additional 10 ml of cold toluene, filtered and washed with 2 ml cold toluene and 4 ml 50% hexane toluene. The sample is dried 4 hrs in vacuo affording 1.9 g (analysis by HPLC assay) of 79% C-076 B2a and 8.2% B2b. A second crop 1.14 g of crystalline B2 material is obtained from the hexane toluene mixture of mother liquor. 68% B2a 9% B2b.

EXAMPLE 11

1.1 grams of the second crop of material from Example 10 is dissolved in 1 ml of methanol and diluted to 20 ml with an 80:20 methanol water system. The solution is applied to a one liter column RP 18 Lichoprep C18 silica-gel 25-40μ 5.5 cm×46 cm. This column had been previously equilibrated with the 80:20 methanol water system. A 400 ml forecut is collected and discarded. With a flow rate of 10.6 ml per minute 26.2 ml cuts were taken, fractions 20-36 representing an eluant volume of 905 to 1354 ml and fractions 37-45 (1355 to 1592 ml) were collected and concentrated to dryness.

EXAMPLE 12

14 mg of fractions 20-36 from Example 11 is dissolved in 1 ml of methylene chloride and passed through 2 g E. Merck Silica Gel 60 (70-230 mesh) wet with methylene chloride. The column is washed with 4 ml of methylene chloride followed by 75 ml mixture of 78.75 parts diethyl ether, 20 parts toluene and 1.25 parts methanol. The material is eluted with a solvent mixture consisting of 77 parts diethylether, 20 parts toluene and 3 parts methanol. Five microliters of each cut is applied to E. Merck Silica Gel 60 F254 plate and the components determined by thin layer chromatography (tlc) with a 9:9:1 system chloroform, ethylacetate:methylalcohol. Based on the tlc results the cuts were pooled representing a total effluent volume of 85 through 105 milliliters. Yield 1.75 mg $R_f$ 0.23 by TLC and a retention time of 134 seconds by HPLC assay. When compared to a standard of B2a the relative mobility (Rm B2a) by TLC was 0.49 and by HPLC was 0.46. This is the compound of the instant invention wherein R is hydrogen.

EXAMPLE 13

12 mg of fractions 37-45 of Example 11 is chromatographed on 2 grams of E. Merck Silica Gel 60 (70-230 mesh) suspended in methylene chloride. The column is washed with 18 ml of methylene chloride and developed with a mixture consisting of 78.75 parts diethylether, 20 parts toluene and 1.25 parts methyl alcohol. The material is eluted in fractions 13-18 representing 36-51 ml of eluent for a yield of 2.5 mg. This material had an $R_f$ of 0.41 by tlc (9:9:1 chloroform:ethyl acetate:methyl alcool system) on F 254 E. Merck Silica 60. When compared to the C-076 B2a standard it had a relative mobility of 0.9. This compound had a 178 sec retention time by HPLC assay RmB2a=0.66. This is the compound of the instant invention wherein R is methyl.

What is claimed is:

1. A compound having the formula:

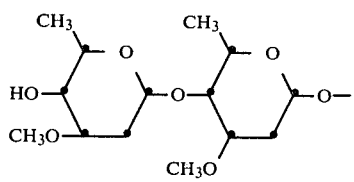

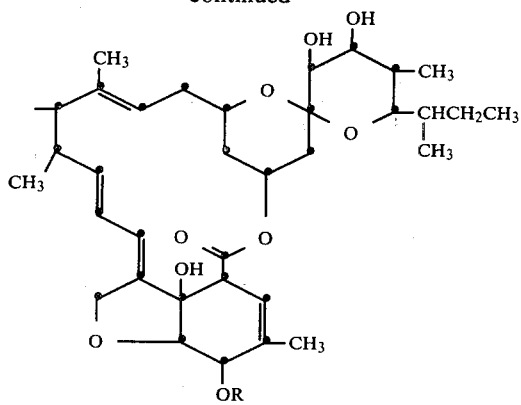

wherein R is hydrogen or methyl.

2. The compound of claim 1 wherein R is hydrogen.
3. The compound of claim 1 wherein R is methyl.
4. A composition useful for the treatment of helminth, acarid, nematode and insect infections which comprises an inert carrier having an effective amount of one or more of the compounds of claim 1 incorporated therein.
5. A method for the treatment of helminth, acarid, nematode and insect infections which comprises administering to an animal infected with parasitic infection, an effective amount of one or more of the compounds of claim 1.

* * * * *